United States Patent [19]
Desai

[11] Patent Number: 5,498,614
[45] Date of Patent: Mar. 12, 1996

[54] BRIDGED AZA-BICYCLIC DERIVATIVES AS SUBSTANCE P ANTAGONIST

[75] Inventor: Manoj C. Desai, Emeryville, Calif.

[73] Assignee: Pfizer Inc., New York, N.Y.

[21] Appl. No.: 335,726

[22] PCT Filed: Feb. 23, 1993

[86] PCT No.: PCT/US93/01429

§ 371 Date: Nov. 7, 1994

§ 102(e) Date: Nov. 7, 1994

[87] PCT Pub. No.: WO93/23380

PCT Pub. Date: Nov. 25, 1993

Related U.S. Application Data

[63] Continuation of Ser. No. 885,110, May 18, 1992, abandoned.

[51] Int. Cl.$^6$ .......................... A61K 31/44; C07D 221/22
[52] U.S. Cl. ..................... 514/299; 514/216; 514/278; 540/477; 540/582; 546/18; 546/112; 546/183
[58] Field of Search .......................... 546/112, 18, 183; 540/477, 582; 514/299, 216, 278

[56] References Cited

U.S. PATENT DOCUMENTS

| | | | |
|---|---|---|---|
| 3,560,510 | 2/1971 | Warawa et al. | 546/137 |
| 4,358,446 | 11/1982 | Haken et al. | 546/337 |
| 4,552,960 | 11/1985 | Krumkalns et al. | 544/336 |
| 4,680,283 | 7/1987 | Veber et al. | 514/17 |
| 5,138,060 | 8/1992 | Godek et al. | 546/133 |
| 5,162,339 | 11/1992 | Lowe | 546/136 |

FOREIGN PATENT DOCUMENTS

| | | |
|---|---|---|
| 0015628 | 9/1980 | European Pat. Off. |
| 0100158 | 2/1984 | European Pat. Off. |
| WO92/06079 | 4/1992 | WIPO |
| WO92/12151 | 7/1992 | WIPO |
| WO92/15585 | 9/1992 | WIPO |
| WO92/17449 | 10/1992 | WIPO |
| WO93/00330 | 1/1993 | WIPO |
| WO93/00331 | 1/1993 | WIPO |
| WO92/01688 | 2/1993 | WIPO |

OTHER PUBLICATIONS

E. J. Warawa et al., "Quinuclidine Chemistry", J. Med. Chem., 18, 587 (1975).
Sandberg et al., "Substance P", J. Med. Chem., 25, 1009, (1982).
P. J. Goadsby et al., "Release of Vasoactive Peptides", Ann. Neurol., 23, 193 (1988).
Regoli, "Neurokinin Agonists & Antagonists", Elsevier Scientific Publishers, Amsterdam, pp. 85–95 (1987).
L. S. Trifonov et al., "Synthesis of 1,2–Five–Ring–Annellated Barrelesnes", Halvetica Chimica Acta, 70, 4, 1732–1736 (1987).
A. S. Yanni et al., "Synthesis & Biological Activity", Indian J. Chem., 21B (7), 705–6, (1982).
Y. P. Gupta et al., "Synthesis of 2, 12–Diazachrysene via Benzene Cyclization Reaction", Indian J. Chem., 19B (5), 400–1, (1980).
V. N. Gogte et al., "Infrared Spectral Study of the Effect of Substitution on Conformation and Hydrogen Bonding in 3–(aryl–amino)propanols", Indian J. Chem., 17B (3), 230–2, (1979).
S. V. Kessar et al., "New Routes to Condensed Polynuclear Compounds", Tetrahedron, 29, Pergamon Press, (GB), 419–424 (1973).
G. N. Walker et al., "Synthesis of Carried Heterocyclic & Substituted Arylalkyl", J. Med. Chem., 9, No. 4, (1966), 624–630.
G. N. Walker et al., "Applicaiton of Sodium Borohydride", Journal of Organic Chemistry, 26, No. 8, (1961), American Chemical Society, (US), 2740–2747.
Suman Rakhit et al., "Formation of Animals form Amines via Pummerer Rearrangement", Can. J. Chem., 57, No. 10, 1153 (1979).

*Primary Examiner*—Bernard Dentz
*Attorney, Agent, or Firm*—Peter C. Richardson; Paul H. Ginsburg; Garth Butterfield

[57] ABSTRACT

The invention relates to bridged aza-bicyclic derivatives of formula (I). These compounds are useful in the treatment of inflammatory and central nervous system disorders, as well as other disorders. Also disclosed are intermediates used in the synthesis of compound of formula (I).

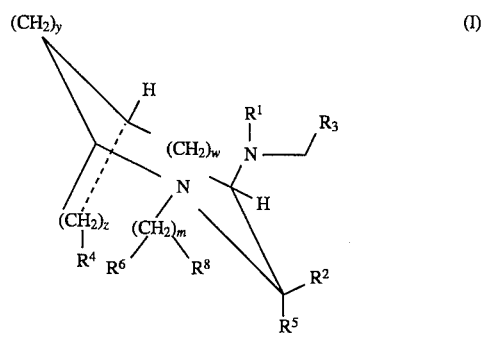

14 Claims, No Drawings

BRIDGED AZA-BICYCLIC DERIVATIVES AS SUBSTANCE P ANTAGONIST

This application is a 371 of PCT/US93/01429, which is a continuation of 07/885,110 filed May 18, 1992, now abandoned.

BACKGROUND OF THE INVENTION

The present invention relates to novel bridged aza-bicyclic derivatives as Substance receptor and related compounds, pharmaceutical compositions comprising such compounds and the use of such compounds in the treatment and prevention of inflammatory and central nervous system disorders, as well as several other disorders. The pharmaceutically active compounds of this invention are substance receptor. This invention also relates to novel intermediates used in the synthesis of such substance receptor.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B.E.B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

Attempts have been made to provide antagonists for substance P and other tachykinin peptides in order to more effectively treat the various disorders and diseases listed above. The few such antagonists thus far described are generally divided between peptide-like and non peptide-like in nature. Peptide-like antagonists are too labile from a metabolic point of view to serve as practical therapeutic agents in the treatment of disease. Non-peptidic antagonists of the present invention, on the other hand, do not possess this drawback, being far more stable from a metabolic point of view than the agents referred to above.

Quinuclidine derivatives and related compounds that exhibit activity as substance P receptor antagonists are referred to in PCT Patent Application PCT/US89/05338, filed Nov. 20, 1989, U.S. patent application Ser. No. 557,442 filed Jul. 23, 1990, PCT application PCT/US91/02853 filed on Apr. 25, 1991 PCT application PCT/US91/03369 filed on May 14, 1991.

Monocyclic piperdine compounds are referred to in European Patent Publication 0,436,334 published on Jul. 10, 1990.

Piperdine derivatives and related heterocyclic nitrogen containing compounds that are useful as substance receptor are referred to in U.S. patent application Ser. No. 590,423 filed Sep. 28, 1990, U.S. patent application Ser. No. 717,943 filed on Jun. 20, 1991, and U.S. patent application Ser. No. 724,268 filed Jul. 1, 1991. Non-peptidic antagonists have also been described in published European patent application 0436334.

SUMMARY OF THE INVENTION

The present invention relates to compounds of the formula

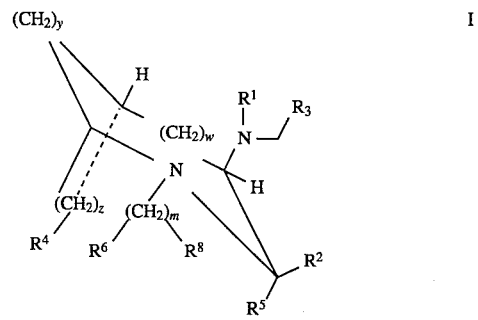

wherein m is an integer from 0 to 8, and any one of the carbon-carbon single bonds of $(CH_2)_m$ may optionally be replaced by a carbon-carbon double bond or a carbon-carbon triple bond, and any one of the carbon atoms of said $(CH_2)_m$ may optionally be substituted with $R^8$;

w is an integer form 0 to 2;

y is an integer from 1 to 4;

z is an integer from 1 to 4, wherein any one of the carbon atoms of said $(CH_2)_z$ may optionally be substituted with $R^4$;

$R^1$ is hydrogen or $(C_1–C_8)$ alkyl optionally substituted with hydroxy, alkoxy or fluoro;

$R^2$ is a group selected from hydrogen, $(C_1–C_6)$ straight or branched alkyl, $(C_3–C_7)$cycloalkyl wherein one of the carbon atoms may optionally be replaced by nitrogen, oxygen or sulfur; aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; phenyl$(C_2–C_6)$alkyl, benzhydryl and benzyl, wherein one of the phenyl moieties of said benzhydryl may optionally be replaced by naphthyl, thienyl, furyl or pyridyl and wherein each of said aryl and heteroaryl groups and the phenyl moieties of said benzyl, phenyl$(C_2–C_6)$alkyl and benzhydryl may optionally be substituted with one or more substituents independently selected from halo, nitro, $(C_1–C_6)$alkyl, $(C_1–C_6)$alkoxy, trifluoromethyl, amino, $(C_1–C_6)$-alkyamino,

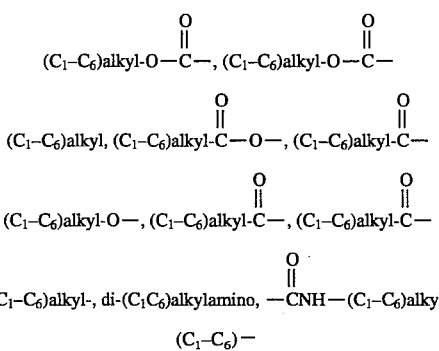

-continued

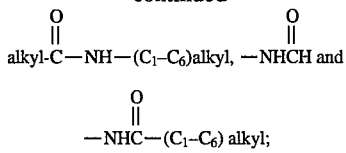

$R^5$ is hydrogen, phenyl or $(C_1–C_6)$alkyl;

or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;

$R^3$ is aryl selected from phenyl, indanyl, and naphthyl; heteroaryl selected from thienyl, furyl, pyridyl, thiazolyl; isothiazolyl, oxazolyl, isoxazolyl, triazolyl, tetrazolyl and quinolyl; or cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3–C_7)$ cycloalkyl may optionally be substituted with one or two substituents, each of said substituents being independently selected from halo, nitro, $(C_1–C_6)$alkyl optionally substituted with from one to three fluorine atoms, $(C_1–C_6)$alkoxy optionally substituted with from one to three fluorine atoms, trifluoromethyl, phenyl, amino, $(C_1–C_6)$alkylamino,

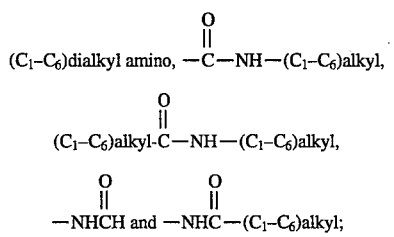

$R^4$ is independently selected from hydrogen, hydroxy, halo, amino, oxo (=O), nitrile, $(C_1–C_6)$alkylamino, di-$(C_1–C_6)$alkylamino, $(C_1–C_6)$alkoxy,

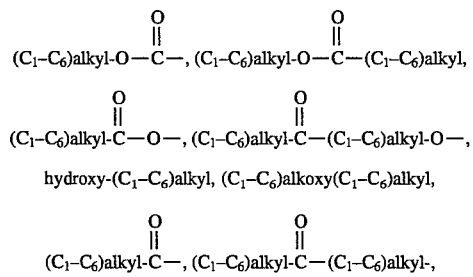

and the groups set forth in the definition or $R^2$;
$R^6$ is

$NHCH_2R^9$, $NHSO_2R^9$ or one of the groups set forth in any of the definitions of $R^2$ and $R^4$;
$R^8$ is oximino (=NOH) or one of the groups set forth in any of the definitions of $R^2$ and $R^4$;
$R^9$ is $(C_1–C_6)$alkyl, hydrogen, phenyl or phenyl $(C_1–C_6)$alkyl;
with the proviso that (a) when m is O, $R^8$ is absent, (b) neither $R^4$, $R^6$, nor $R^8$ can form, together with the carbon to which it is attached, a ring with $R^5$, (c) the sum of y and z must be less than 7.

Preferred compounds of formula I are those wherein m, w, y, z, $R^3$, $R^4$, $R^5$, $R^6$, and $R^8$ are defined as above and $R^2$ is a radical selected from phenyl, naphthyl and benzhydryl; wherein each of said phenyl, naphthyl and benzhydryl may optionally be substituted with one or more substituents independently selected from halo, nitro, $(C_1–C_6)$alkyl, $(C_1–C_6)$alkoxy, trifluoromethyl, amino, $(C_1–C_6)$-alkylamino,

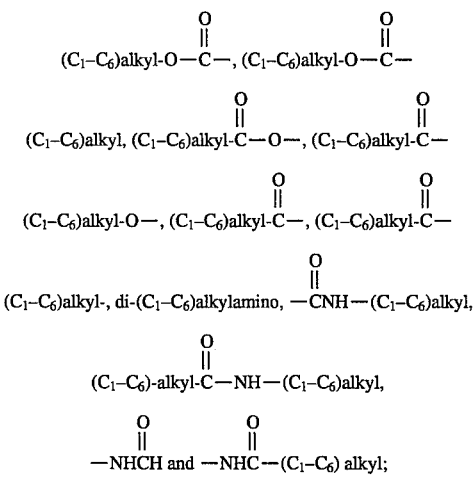

and wherein one of the phenyl moieties of said benzhydryl may optionally be replaced by naphthyl, thienyl, furyl or pyridyl.

The present invention also relates to compounds of formula I wherein m, w, y, z, $R^3$, $R^5$, $R^6$ and $R^8$ are defined as above; and $R^2$ is a group selected from hydrogen, phenyl, naphthyl and benzhydryl; wherein each of said phenyl, naphthyl and benzhydryl may optionally be substituted with one or more substituents independently selected from halo, nitro, $(C_1–C_6)$ alkyl, $(C_1–C_6)$alkoxy, trifluoromethyl, amino, $(C_1–C_6)$-alkylamino,

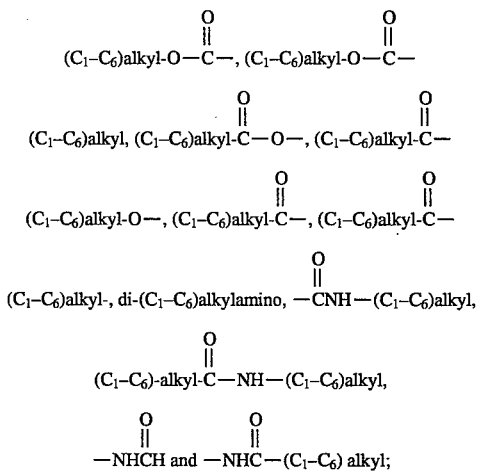

and wherein one of the many phenyl moieties of said benzhydryl may optionally be replaced by naphthyl, thienyl, furyl or pyridyl; and $R^4$ is independently selected from hydrogen, hydroxy, halo, amino, oxo (=O), nitrile, $(C_1–C_6)$alkylamino, di-$(C_1–C_6)$alkylamino, $(C_1–C_6)$alkoxy,

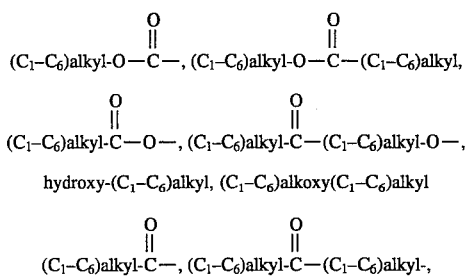

$(C_1-C_6)$alkyl and phenyl.

A preferred compound of the formula I is (3RS,4RS)-3-phenyl-4-(2-methoxybenzyl)amino-2-azabicyclo-[3.3.1]nonane.

Other compounds of the present invention include:
(3RS,4RS)-3-phenyl-4-(2methoxybenzyl)amino-2-azabicyclo[3.3.1]nonane;
(3RS,4RS)-3-phenyl-4-(5-chloro-2-methoxybenzy)amino-2-azabicyclo[3.3.1]nonane;
(3RS,4RS)-3-phenyl -4-(2,5-dimethoxybenzyl)amino-2-azabicyclo[3.3.1]nonane;
(3RS,4RS)-3-phenyl-4-(3,5-difluoro-2-methoxybenzyl)amino-2-azabicyclo[3.3.1]nonane;
(3RS,4RS)-3-phenyl-4-(5-fluoro-2-methoxybenzyl)amino-2-azabicyclo[3.3.1]nonane;
(3RS,4RS)-3-phenyl-4-(5-trifluoromethoxy-2-methoxybenzyl)amino-2-azabicyclo[3.3.1]nonane;
(3RS,4RS)-3-phenyl-4-(5-methyl-2-methoxybenzyl)amino-2-azabicyclo[3.3.1]nonane;
(3RS,4RS)-3-phenyl-4-(5-trifluoromethyl-2-methoxybenzyl)amino-2-azabicyclo[3.3.1]nonane;
(3RS,4RS)-3-phenyl-4-(2-methoxybenzyl)amino-2-azabicyclo[3.2.1]octane;
(3RS,4RS)-3-phenyl-4-(5-chloro-2-methoxybenzyl)amino-2-azabicyclo[3.2.1]octane;
(3RS,4RS)-3-phenyl-4-(2,5-dimethoxybenzyl)amino-2-azabicyclo[3.2.1]octane;
(3RS,4RS)-3-phenyl-4-(3,5-difluoro-2-methoxybenzyl)amino-2-azabicyclo[3.2.1]octane;
(3RS,4RS)-3-phenyl-4-(5-fluoro-2methoxybenzyl)amino-2-azabicyclo[3.2.1]octane;
(3RS,4RS)-3-phenyl-4-(5-trifluoromethoxy-2-methoxybenzyl)amino-2-azabicyclo[3.2.1]octane;
(3RS,4RS)-3-phenyl-4-(5, trifluoromethyl-2-methoxybenzyl)amino-2-azabicyclo[3.2.1]octane;
(3RS,4RS)-3-phenyl-4-(5-methyl-2-methoxybenzyl)amino-2-azabicyclo [3.2.1]octane;
(3RS,4RS)-3-phenyl-4-(2-methoxybenzyl)amino-8-methyl-2-azabicyclo[3.3.1]nonane;
(3RS,4RS,8SR)-3-phenyl-4-(5-chloro-2-methoxybenzyl)amino-8-methyl-2-azabicyclo[3.3.1]nonane;
(3RS,4RS,8SR)-3-phenyl-4- (2,5-dimethoxybenzyl)amino-8-methyl-2-azabicyclo[3.3.1]nonane;
(3RS,4RS,8SR)-3-phenyl-4-(3,5-difluoro-2-methoxybenzyl)amino-8-methyl-2-azabicyclo[3.3.1]nonane;
(3RS,4RS,8SR)-3-phenyl-4-(5-fluoro-2-methoxybenzyl)amino-8-methyl-2azabicyclo[3.3.1]nonane;
(3RS,4RS,8SR)-3-phenyl-4-(5-trifluoromethoxy-2-methoxybenzyl)amino8-methyl-2-azabicyclo[3.3.1]nonane;
(3RS,4RS,8SR)-3-phenyl-4-(5-methyl-2-methoxybenzyl)amino-8-methyl-2-azabicyclo[3.3.1]nonane;
(3RS,4RS,8SR)-3-phenyl-4-(5-trifluoromethyl-2-methoxybenzyl)amino-8-methyl-2-azabicyclo[3.3.1]nonane;
(3RS,4RS,7SR)-3-phenyl-4-(2-methoxybenzyl)amino-7-methyl-2-azabicyclo[3.2.1]octane;
(3RS,4RS,7SR)-3-phenyl-4-(5-chloro-2-methoxybenzyl)amino-7-methyl-2-azabicyclo[3.2.1]octane;
(3RS,4RS,7SR)-3-phenyl-4(2,5-dimethoxybenzyl)amino-7-methyl-2-azabicylco[3.2.1]octane;
(3RS,4RS, 7SR)-3-phenyl-4-(3,5-difluoro-2-methoxybenzyl)amino-7-methyl-2azabicyclo[3.2.1]octane;
(3RS,4RS,7SR)-3-phenyl-4-(5-fluoro-2-methoxybenzyl)amino-7-methyl-2-azabicyclo[3.2.1]octane;
(3RS,4RS,7SR)-3-phenyl-4-(5-trifluoromethoxy-2-methoxybenzyl)amino-7-methyl-2-azabicyclo[3.2.1]octane;
(3RS,4RS,7SR)-3-phenyl-4-(5-trifluoromethyl-2-methoxybenzyl)amino-7-methyl-2-azabicyclo[3.2.1]octane;
(3RS,4RS,7SR)-3-phenyl-4-(5-methyl-2-methoxybenzyl)amino-7-methyl-2-azabicyclo[3.2.1]octane;
(3RS,4RS,8SR)-3-phenyl-4-(2-methoxybenzyl)amino-8-carbomethoxy-2-azabicyclo[3.3.1]nonane;
(3RS,4RS,8SR)-3-phenyl-4-(5-chloro-2-methoxybenzyl)amino-8-carbomethoxy-2-azabicyclo[3.3.1]nonane;
(3RS,4RS,8SR)-3-phenyl-4-(2,5-dimethoxybenzyl)amino-8-carbomethoxy-2-azabicyclo[3.3.1]nonane;
(3RS,4RS,8SR)-3-phenyl-4-(3,5-difluoro-2-methoxybenzyl)-amino-8-carbomethoxy-2-azabicyclo[3.3.1]nonane;
(3RS,4RS,8SR)-3-phenyl-4-(5-fluoro-2-methoxybenzyl)amino-8-carbomethoxy-2-azabicyclo[3.3.1]nonane;
(3RS,4RS,8SR)-3-phenyl-4-(5-trifluoromethoxy-2-methoxybenzyl)amino-8-carbomethoxy-2-azabicyclo[3.3.1]nonane;
(3RS,4RS,8SR)-3-phenyl-4-(5-methyl-2-methoxybenzyl)amino-8-carbomethoxy-2-azabicyclo[3.3.1]nonane;
(3RS,4RS,8SR)-3-phenyl-4-(5-trifluoromethyl-2-methoxybenzyl)amino-8-carbomethoxy-2-azabicyclo[3.3.1]nonane;
(3RS,4RS,7SR)-3-phenyl-4-(2-methoxybenzyl)amino-7-carbomethoxy-2-azabicyclo[3.2.1]octane;
(3RS,4RS,7SR)-3-phenyl-4-(5-chloro-2-methoxybenzyl)amino-7-carbomethoxy-2-azabicyclo[3.2.1]octane;
(3RS,4RS,7SR)-3-phenyl-4-(2,5-dimethoxybenzyl)amino-7-carbomethoxy-1-azabicyclo[3.2.1]octane;
(3RS,4RS,7SR)-3-phenyl-4-(3,5-difluoro-2-methoxybenzyl)amino-7-carbomethoxy-2-azabicyclo[3.2.1]octane;
(3RS,4RS,7SR)-3-phenyl-4-(5-fluoro-2-methoxybenzyl)amino-7-carbomethoxy-2-azabicyclo[3.2.1]octane;
(3RS,4RS,7SR)-3-phenyl-4-(5-trifluoromethoxy-2-methoxybenzyl)amino-7-carbomethoxy-2-azabicyclo[3.2.1]octane;
(3RS,4RS,7SR)-3-phenyl-4-(5-trifluoromethyl-2-methoxybenzyl)amino-7-carbomethoxy-2-azabicyclo[3.2.1]octane;
(3RS,4RS,7SR)-3-phenyl-4-(5-methyl-2-methoxybenzyl)amino-7-carbomethoxy-2-azabicyclo[3.2.1]octane;
(3RS,4RS,8SR)-3-phenyl-4-(2-methoxybenzyl)amino-8-carboxy-2-azabicyclo[3.3.2]nonane;
(3RS,4RS,8SR)-3-phenyl-4-(5-chloro-2-methoxybenzyl)amino-8-carboxy-2-azabicyclo[3.3.1]nonane;
(3RS,4RS,8SR)-3-phenyl-4-(2,5-dimethoxybenzyl)amino-8-carboxy-2-azabicyclo[3.3.1]nonane;
(3RS,4RS,8SR)-3-phenyl-4-(3,5-fluoro-2-methoxybenzyl)amino-8-carboxy-2-azabicyclo[3.3.1]nonane;
(3RS,4RS,8SR)-3-phenyl-4-(5-fluoro-2-methoxybenzyl)amino-8-carboxy-2-azabicyclo[3.3.1]nonane;
(3RS,4RS,8SR)-3-phenyl-4-(5-trifluoromethoxy-2-methoxybenzyl)amino-8-carboxy-2-azabicyclo[3.3.1]nonane;
(3RS,4RS,8SR)-3-phenyl-4-(5-methyl-2-methoxybenzyl)amino-8-carboxy-2azabicyclo[3.3.1]nonane;
(3RS,4RS, 8SR)-3-phenyl-4-(5-trifluoromethyl-2-methoxybenzyl)amino-8-carboxy-2-azabicyclo[3.3.1]nonane;
(3RS,4RS,7SR)-3-phenyl-4-(2-methoxybenzyl)amino-7-carboxy-2-azabicyclo[3.2.1]octane;
(3RS,4RS,7SR)-3-phenyl-4-(5-chloro-2-methoxybenzyl)amino-7-carboxy-2-azabicyclo[3.2.1]octane;

(3RS,4RS,7SR)-3-phenyl-4-(3,5-difluoro-2-methoxybenzyl)amino-7-carboxy-2-azabicyclo[3.2.1]octane;
(3RS,4RS,7SR)-3-phenyl-4-(5-fluoro-2-methoxybenzyl)amino-7-carboxy-2-azabicyclo[3.2.1]octane;
(3RS,4RS,7SR)-3-phenyl-4-(5-trifluoromethoxy-2-methoxybenzyl)amino-7-carboxy-2-azabicyclo[3.2.1]octane;
(3RS,4RS,7SR)-3-phenyl-4-(5-trifluoromethyl-2-methoxybenzyl)amino-7-carboxy-2-azabicyclo[3.2.1]octane; and
(3RS,4RS,7SR)-3-phenyl-4-(5-methyl-2-methoxybenzyl)-amino-7-carboxy-2-azabicyclo[3.2.1]octane;

The present invention also relates to compounds of the formula

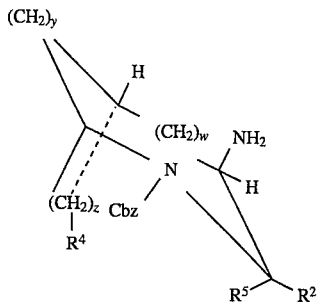

IV wherein w, y, z, $R^2$, $R^4$, $R^5$, and $R^7$ are defined as above.

The compounds of formula IV are novel intermediates used in the synthesis of compounds of formula I.

A preferred compound of formula IV is (3RS,4RS)-2-(benzyloxycarbonyl)-3-phenyl-4-amino-2-azabicyclo[3.3.1]nonane.

The present invention also relates to compounds of the formula

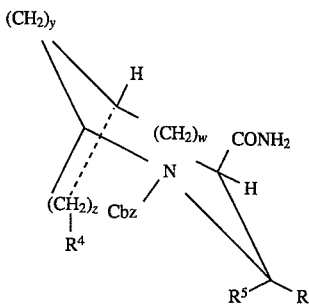

V wherein w, y, z, $R^2$, $R^4$, and $R^5$ are defined as above. The compounds of formula V are novel intermediates used in the synthesis of compounds of formula I.

A preferred compound of formula V is (3RS,4RS)-2-(benzyloxycarbonyl)-3-phenyl-4-carboxamide-2-azabicyclo[3.3.1]nonane.

The present invention also relates to compounds of the formula

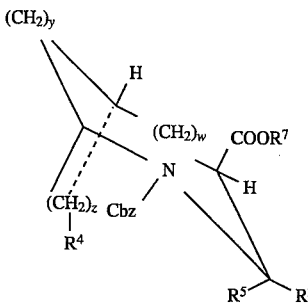

VI wherein w, y, z, $R^2$, $R^4$, and $R^5$ are defined as above and $R^7$ is selected from the group H, alkyl ($C_1$–$C_6$) branched or unbranched. The compounds of formula VI are novel intermediates used in the synthesis of compounds of formula I.

A preferred compound of formula VI is (3RS,4RS)-2-(benzyloxycarbonyl)-3-phenyl-2-azabicyclo-[3.3.1]nonane-4-carboxylic acid, methyl ester.

The present invention also relates to compounds of the formula

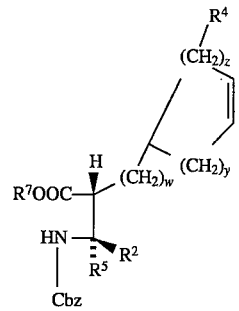

VII wherein w, y, z, $R^2$, and $R^5$ are as defined for compounds of formula I and $R^7$ is selected from hydrogen and ($C_1$–$C_6$) alkyl. The compounds of formula VII are novel intermediates used in the synthesis of compounds of formula I.

The present invention also relates to compounds of the formula

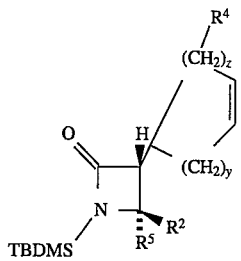

VIII wherein w, y, z, $R^2$, $R^4$, $R^5$ and $R^7$ are as defined for compounds of formula I. The compounds of formula VIII are novel intermediates used in the synthesis of compounds of the formula I.

The term "halo," as used herein, unless otherwise indicated, includes chloro, fluoro, bromo and iodo.

The term "alkyl," as used herein, unless otherwise indicated, includes saturated monovalent hydrocarbon radicals having straight or branched or cyclic moieties or combinations thereof.

The term "one or more substituents," as used herein, includes from one to the maximum number of substituents possible based on the number of available bonding sites.

Formula I above includes compounds identical to those depicted but for the fact that one or more hydrogen atoms are replaced by radioactive isotopes thereof. Such radiolabelled compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain and in vivo binding in the relevant tissues for inflammation, e.g., immune-type cells or cells that are directly involved in inflammatory bowel disorders and the like.

The present invention also relates to a pharmaceutical composition for treating or preventing a condition selected from the group consisting of inflammatory diseases (e.g., arthritis, psoriasis, asthma and inflammatory bowel disease), reflux gastroesophogal disease, hypertension, anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), reflux gastroesophogal disease, hypertension, anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), reflux gastroesophogal disease, hypertension, anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), reflux gastroesophogal disease, hypertension, anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric and diasteriomeric forms. This invention relates to all optical isomers and all stereoisomers of compounds of the formula I, and mixtures thereof.

Formula I above includes compounds identical to those depicted but for the fact that one or more hydrogen or carbon atoms are replaced by radioactive isotopes thereof. Such radiolabelled compounds are useful as research and diagnostic tools in metabolism pharmacokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like. Included among the radiolabelled forms of compounds of the formula I are the tritium and $C^{14}$ isotopes thereof.

DETAILED DESCRIPTION OF THE INVENTION

The compounds of the formula I may be prepared as described in the following reaction scheme and discussion. Unless otherwise indicated, m, w, y, z, $R^1$, $R^2$, $R^3$, $R^4$, $R^5$, $R^6$, $R^7$, $R^8$ and $R^9$ in the reaction schemes and discussion that follow are defined as above.

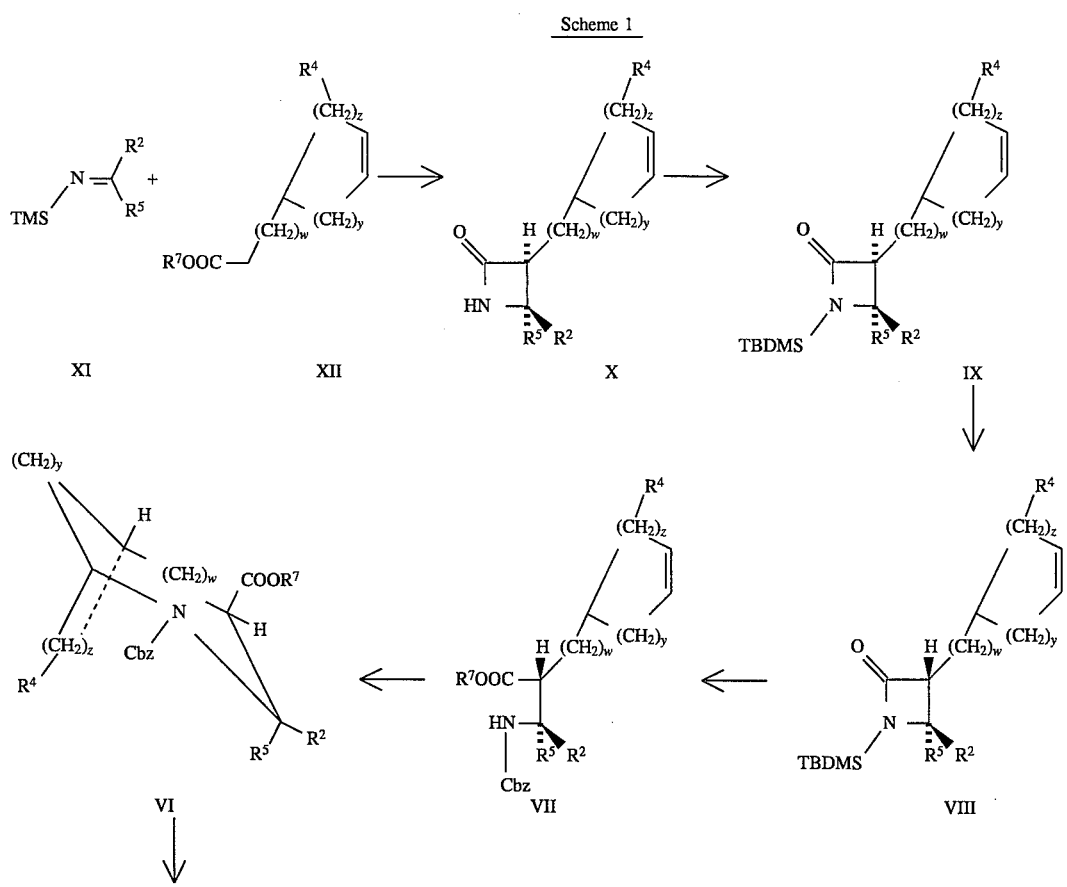

Scheme 1

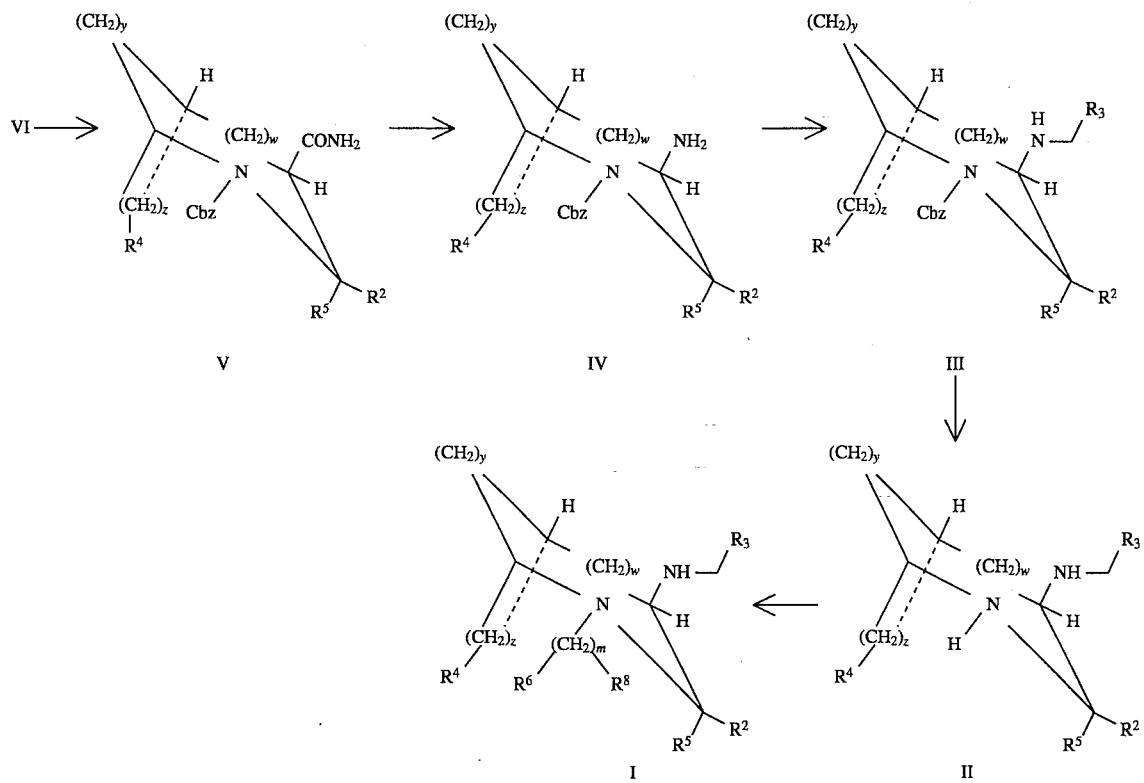

Scheme 1 illustrates a method of preparing compounds of the formula I. Referring to scheme 1, a compound of the formula XII is reacted with a compound having the formula

wherein $R^2$ and $R^5$ are defined as above. This reaction is generally carried out by adding the compound of formula XII in tetrahydrofuran to lithium diisopropylamide monotetrahydrofuran at a temperature from about −78° C. to about −50° C., stirring the resulting mixture for about 0.25 to about 10 hours, and then adding the compound of formula XI to the mixture at approximately the same temperature over a period of about 5 minutes to about 1 hour. This reaction produces a β-lactam of the formula X.

A compound of the formula X is reacted with a nitrogen-protecting reagent such as t-butyldimethylsilyl chloride (TBDMS-Cl), t-butyldimethylsilyl triflate (TBDMS-OTf) or benzyl bromide/t-butoxide, preferably TBDMS-Cl, to form a compound of the formula IX. This reaction is typically carried out in a polar solvent such as DMF or triethylamine, preferably triethylamine, at a temperature of from about 0° to about 140° C. Room temperature is preferred.

The hydrogen at carbon 3 of the cis amide protected lactam of formula IX then is stereochemically inverted by addition of a strong base and quenching the anion with a proton source, preferably acetic acid, to form the 2,3 trans isomer of the amide protected lactam. This isomerization converts the cis lactam to the thermodynamically more stable trans form of formula VIII. The solvent should be inert and solvent polarity can vary in a broad range. Examples of appropriate solvents are tetrahydrofuran, hexane and toluene.

The β lactam of formula VIII is converted into the compound of formula VII by simultaneous removal of the TBDMS group and cleavage of the β-lactam. This process is typically conducted using a concentrated acid such as concentrated sulfuric or perchloric acid, preferably sulfuric acid, in a polar solvent such as a lower alcohol, preferably methanol, for about 0.5 to about 16 hours. Suitable reaction temperatures range from about room temperature to about 150° C., with the reflux temperature of the solvent being preferred. The product of this reaction is a compound having a structure similar to that of formula VII, except that the N-carbobenzyloxy group is replaced by hydrogen. Treatment of this compound with benzylchloroformate to produce a compound of the formula VII having the same stereochemistry is generally carried out in a polar solvent such as water, water/acetone, chloroform, dichloroethane or ethyl acetate in the presence of a base. Examples of bases that may be used are triethylamine, sodium bicarbonate and potassium bicarbonate. This reaction may be conducted at temperatures from about 0° C. to about 100° C., for a period of about 5 minutes to about 18 hours. Preferably, it is conducted at about 25° C.

The compound of formula VII may be cyclized to form the corresponding compound having the formula VI and the same stereochemistry with respect to the carbons to which $R^2$, $R^5$ and $COOR^7$ are attached, by first reacting it with mercuric trifluoroacetate, mercuric chloride or mercuric acetate, and then reacting the product of such reaction with sodium borohydride, lithium triacetoxyborohydride or a similar reducing agent. The reaction with the mercury salt is usually conducted in a polar solvent at a temperature from about −78° C. to about 25° C. Suitable solvents include tetrahydrofuran, acetonitrile and nitromethane. Reduction is carried out preferably using sodium borohydride in tetrahydrofuran at about 25° C. Reduction with sodium borohydride is generally carried out by adding an aqueous solution of sodium borohydride to the reaction mixture from the foregoing reaction at a temperature from about −78° C. to about 0° C., preferably at about 0° C.

Treatment of the compound of formula VI so formed with about 5 equivalents each of trimethyl aluminum and ammonium chloride in a nonpolar solvent such as benzene or toluene for about 0.5 to about 16 hours yields a compound of the formula V having the same stereochemistry. Reaction temperatures may range from about room temperature to about 100° C., with about 50° C. being preferred.

The conversion of the carboxamide group of the compound of formula V to form a compound of the formula IV having the same stereochemistry may be accomplished by a Hoffmann degradation using reagents such as bromine/sodium methoxide in methanol, lead tetraacetate in t-butyl alcohol, tin (IV) chloride, iodobenzene bis(trifluoroacetate) in aqueous acetonitrile, sodium bromide or benzyltrimethyl ammonium tribromide. Preferably, the compound of formula V is treated with lead tetraacetate in t-butanol. This reaction is typically carried out at a temperature from about room temperature to the reflux temperature of the solvent, preferably at the reflux temperature, for about 15 minutes to about 10 hours, preferably for about 3 to about 5 hours. Reaction of the compound of formula V with an acid such as hydrochloric acid, trifluoroacetic acid or perchloric acid yields a compound of the formula having the same stereochemistry. The solvent is typically a solvent such as methylene chloride, dioxane, ether or tetrahydrofuran, preferably dioxane, ether or tetrahydrofuran, preferably dioxane. This reaction is typically carried out at a temperature from about −10° to about 50° C., preferably at about 25° C., for about 0.5 to 24 hours.

Reductive amination of a compound of the formula $R^3CHO$ in the presence of a compound of the formula IV from the above step yields a compound of the formula III having the same stereochemistry. Examples of reducing agents that may be used are hydrogen in the presence of a metal catalyst, sodium borohydride, sodium cyanoborohydride and sodium triacetoxyborohydride. This reaction is generally carried out in a polar solvent such as acetic acid or a lower alkanol, in the presence of a dehydrating agent such as molecular sieves, at a temperature from about 0° to about 50° C. Methanol is the preferred solvent and 25° C. is the preferred temperature. It is also preferable that the pH of the reaction mixture be about 4 to about 5.

Alternatively, compounds of the formula III may be formed by acylating a compound of the formula IV with a compound having the formula $R^3COCl$, and then reducing the resulting amide. The acylation is generally conducted in a polar solvent (e.g., dichloromethane, tetrahydrofuran or ethyl ether), at a temperature from about 0° to about 60° C. The preferred solvent is dichloromethane and the preferred temperature is about 25° C. Examples of reducing agents that may be used to reduce the amide are lithium aluminum hydride and borane dimethyl sulfide. The reduction is typically carried out in a polar solvent (e.g., ether, tetrahydrofuran or DME) at a temperature from about 0° C. to about the reflux temperature of the solvent, preferably at about room temperature.

The carbobenzoxy group, (CBZ), is then removed by reacting it with ammonium formate in the presence of palladium on charcoal (e.g., 10% palladium on charcoal) to form a compound of formula II. Usually, a polar solvent such as ethyl acetate or a lower alkanol is used, and the reaction is run at a temperature from about room temperature to about 150° C. for about 0.5 to about 24 hours. Preferably, the reaction is conducted in ethanol at room temperature for about 3 to about 24 hours.

The compound of formula II so formed may be converted to a compound of the formula I having the same stereochemistry, as illustrated in scheme 1, by reacting it with a compound of the formula

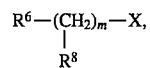

wherein X is halo, wherein one of the carbon-carbon single bonds of said $(CH_2)_m$ may optionally be replaced by a carbon-carbon double bond, and wherein one of the carbons of said $(CH_2)_m$ may optionally be substituted with $R^8$. This reaction is typically carried out in the presence of a base such as triethylamine or potassium t-butoxide, in a polar solvent such as methylene chloride or dichloroethane, and at a temperature from about room temperature to about 150° C. Preferably, the reaction is carried out at the reflux temperature in methylene chloride in the presence of triethylamine.

The novel compounds of the formula I and the pharmaceutically acceptable salts thereof are useful as substance receptor, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance receptor for the control and/or treatment of any of the aforesaid clinical conditions in mammals, including humans.

The compounds of the formula I and the pharmaceutically acceptable salts thereof hereafter, referred to as the active compounds of the invention can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to treatment, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance receptor is determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 µg/ml of leupeptin, 2 µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders may be determined primarily by a study of their ability to suppress substance P-induced or substance P agonist induced hypermotility in guinea pigs.

This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

A.
cis-3-(3-Cyclohexenyl)-4-phenyl-1-azetidin-2-ones

To a cooled solution of lithium bis(trimethylsilyl)-amide (1.0M in tetrahydrofuran (THF), 91 milliliter, 91 millimoles) at −78° C. was added benzaldehyde (8.57 milliliter, 84 millimoles) and further stirred for 1 hour. In the meantime, in another flask lithium diisopropylamide-monotetrahydrofuran (1.5M in cyclohexanes, 51.9 milliliter, 78 millimole) in tetrahydrofuran (150 milliliter) was cooled to −78° C. and was then slowly added to a solution of 3-cyclohexane-1-acetic acid, methyl ester (10 grams, 65 millimole) in tetrahydrofuran (100 milliliter). The reaction mixture was further stirred for 1 hour at −78° C. followed by the addition of the contents of the first flask via cannula over a 15 minute period. The cold bath was removed and the mixture was allowed to warm to room temperature (1 hour). The resulting solution was diluted with 100 milliliter of one normal hydrochloric acid (HCl) and stirred for one hour. The resulting solution was extracted with ether (3×350 milliliter). The organic phases were combined and washed with water, dried (anhydrous magnesium sulfate (MgSO$_4$) and concentrated in vacuo to afford a residue which on trituration with ether-pentane afforded cis-3-(3-cyclohexenyl)-4-phenyl-1-azetidin-2-ones as oil (21.1 grams, 100%) which was used as such in the next step.

$^1$H-NMR (CDCl$_3$) δ0.9–2.04 (7H, m), 3.33 (1H, m), 4.8 (1H, t, J=5.4 Hz), 5.2–5.3 (0.5H, m), 5.4–5.65 (1.5H, m), 6.01 (1H, bs), 7.23–7.4 (5H, m).

B. cis-3-(3-Cyclohexenyl)-4-phenyl-1-(tert.-butyldimethyl-silyl)azetidin-2-ones

To a stirred solution of cis-3-(3-cyclohexenyl)-4-phenyl-1-azetidin-2-ones (21.1 grams, 93 millimoles), and diisopropylethyl amine (21.0 milliliter, 120 millimoles) in methylene chloride (300 milliliter) at 0° C. was added tert. butyldimethylsilyl triflate (25.6 milliliter, 111 millimoles). The reaction mixture was further stirred for 15 minute, and then it was diluted with methylene chloride (200 milliliter) and with water. The organic phase was successively washed with 1 normal HCl (1×100 milliliter), 1 normal sodium bicarbonate (NaHCO$_3$) (1×100 milliliter) and water (2×100 milliliter). The methylene chloride layer was dried (anhydrous MgSO$_4$) and filtered which was concentrated under vacuum to afford cis-3-(3-cyclohexenyl)-4-phenyl-1-(tert.-butyldimethylsilyl) azetidin-2-ones (36.6 grams).

$^1$H-NMR (CDCl$_3$) δ0.24 (3H, s), 0.93 (9H, s), 1.1–2.5 (7H, m), 3.4 (1H, m), 4.69 (1H, t, J=5.5 Hz), 5.2–5.3 (0.5H, m), 5.4–5.6 (1.5H, m), 7.23–7.4 (5H, m).

C. trans-3-(3-Cyclohexenyl)-4-phenyl-1-(tert.-butyldimethyl-silyl)azetidin-2-ones To a stirred solution of cis-3-(3-cyclohexenyl)-4-phenyl-1-(tert.-butyldimethylsilyl)azetidin-2-ones (12.23 grams, 36 millimoles) in tetrahydrofuran (125 milliliter) at 78° C., was added lithium diisopropylamide in tetrahydrofuran (1.5M, 33.6 milliliter, 50 millimoles), and the reaction mixture was further stirred for 25 minutes. At the end of this period, the reaction mixture was quenched with acetic acid (5M in tetrahydrofuran, 16 milliliter, 80 millimole) in tetrahydrofuran (50 milliliter) and was warmed to room temperature (~25° C.). Thereafter it was concentrated under vacuum, diluted with 1 normal HCl and extracted with ether (3×150 milliliter). The combined organic layers were washed with water (2×100 milliliter), dried (anhydrous MgSO$_4$) and filtered. The ether was removed under vacuum to afford orange colored oil (17.5 grams) which was loaded on a flash silica gel column. Elution with 5% ethyl ether in hexane afforded pure trans-3-(3-cyclohexenyl)-4-phenyl-1-(tert.-butyldimethylsilyl)azetidin-2-ones (6.25 grams, melting point 66° C., 51%).

$^1$H-NMR (CDCl$_3$) δ0.19 (3H, s), 0.91 (9H, s), 1.1–2.5 (7H, m), 3.01 (1H, m), 4.29 (1H, d, J=2.5 Hz), 5.63 (2H, m), 7.23–7.4 (5H, m).

D. Methyl 2-(3-cyclohexenyl)-3-phenyl-3-(benzyloxycarbonyl)amino-propionates

The solution of trans-3-(3-cyclohexenyl)-4-phenyl-1-(tert.-butyldimethylsilyl)azetidin-2-ones (2.96 grams, 8.7 millimoles) in 5% sulfuric acid in methanol (30 milliliter) was refluxed for 18 hours. At the end of this period, the reaction mixture was cooled and carefully neutralized with powdered sodium bicarbonate. The contents of the flask were concentrated under vacuum and then, after dilution with water (200 milliliter), were extracted with methylene chloride (3×150 milliliter). The combined organic layers were dried (anhydrous MgSO$_4$) and filtered. The solvents were removed under vacuum to afford hydrolyzed product as a brownish oil (2.17 grams, 100%) which was dissolved in ethyl acetate (25 milliliter) and cooled to 0° C. To it aqueous potassium carbonate solution (2M, 21 milliliter, 42 millimole) and benzyl chloroformate (1.31 milliliter, 9.2 millimoles) were added. The reaction mixture was warmed to room temperature and the aqueous layer was extracted with additional ethyl acetate (2×100 milliliter). The combined organic layers were dried (anhydrous MgSO$_4$), filtered and concentrated under vacuum to afford orange oil which loaded on silica gel column. Elution with 20% ethyl acetate in hexane afforded methyl 2-(3-cyclohexenyl)-3-phenyl-3-(benzyloxycarbonyl)-amino-propionates (3.45 grams, <90%).

$^1$H-NMR (CDCl$_3$) δ1.2–2.6 (8H, m), 3.42 (3H, s), 5.0–5.2 (3H, m), 5.5–5.7 (2H, m), 7.1–7.5 (10H, m).

E. (±)-2-(benzyloxycarbonyl)-3-phenyl-2-azabicyclo[3.3.1]nonane-4-carboxylic acid, methyl ester To a stirred solution of methyl 2-(3-cyclohexenyl)-3-phenyl-3-(benzyloxycarbonyl)amino-propionates (3.42 grams, 8.7 millimoles) in acetonitrile (40 milliliter) at 0° C., mercuric trifluoroacetate (5.6 grams, 1.3 millimoles) was added. The reaction mixture was warmed to room temperature and stirred for 48 hours. The reaction mixture was recooled to 0° C. and to it a solution of sodium borohydride (2.0 grams) in water (10 milliliter) was added slowly; it was stirred for 30 minute during which time grey precipitates were formed. At the end of this period the reaction mixture was filtered through diatomaceous earth (Celite (trademark)) and the filtrate was concentrated under vacuum. The residue was suspended in water and extracted with methylene chloride (3×100 milliliter). The combined organic layers were dried (anhydrous MgSO$_4$), filtered and concentrated under vacuum to afford an oil (5.0 grams). This was loaded on a flash SiO$_2$-gel column; elution with 20% ether in hexane afforded (±)-2-(benzyloxycarbonyl)-3-phenyl-2-azabicyclo[3.3.1]nonane-4-carboxylic acid, methyl ester (0.226 grams; 7%).

$^1$H-NMR (CDCl$_3$) δ1.2–1.8 (6H, m), 2.1–2.35 (2H, m), 2.6–2.9 (1H, m), 3.1–3.3 (1H, m), 3.55 (3H, s), 4.0–4.2 (1H, m), 5.1 (2H, m), 5.7–6.15 (1H, m), 7.0–7.4 (10H, m).

F.
(±)-2-(benzyloxycarbonyl)-3-phenyl-4-carboxamide-2-azabicyclo[3.3.1]nonane

To a suspension of ammonium chloride (0.52 gram, 9.6 millimole) in benzene (19 milliliter) at 5° C., was slowly added 2M solution (4.8 milliliter, 9.6 millimole) of trimethyl aluminum in hexane. After the addition was complete, the reaction mixture was allowed to warm to room temperature and was stirred for 45 minutes until gas evolution had ceased. To it a solution of (±)-2-(benzyloxycarbonyl)-3-phenyl-2-azabicyclo[3.3.1]nonane-4-carboxylic acid, methyl ester (0.76 gram, 1.9 millimole) in benzene (10 milliliter) was added and the solution was maintained at 50°–55° C. for 48 hours. The reaction mixture was cooled to room temperature and was carefully quenched with 5% HCl (3 milliliter). Then the resulting mixture was filtered through diatomaceous earth (Celite (trademark)) and the residue was washed with methylene chloride (200 milliliter). The organic layer was separated while the aqueous layer was made basic and extracted with methylene chloride (200 milliliter). The organic extracts were combined, dried (anhydrous MgSO$_4$) and concentrated in vacuo to afford (±)-2-(benzyloxycarbonyl)-3-phenyl-4-carboxamide-2-azabicyclo[3.3.1]nonane (0.66 gram, 92%).

$^1$H-NMR (CDCl$_3$) δ1.2–2.5 (10H, m), 2.9–3.2 (1H, m), 4.4–4.2 (1H, m), 5.2 (1H, m), 5.4–6.0 (3H, m), 7.15–7.5 (10H, m).

G. (±)-2-(benzyloxycarbonyl)-3-phenyl-4-amino-2-azabicyclo[3.3.1]nonane

To a solution of (±)-2-(benzyloxycarbonyl)-3-phenyl-4-carboxamide-2-azabicyclo[3.3.1]nonane (0.66 gram, 1.8 millimoles) in acetonitrile (9 milliliter) and water (9 milliliter) was added bi[(trifluoroacetoxy)iodo]benzene (0.9 grams, 2.1 millimoles). The reaction mixture was stirred for 18 hours at room temperature and then poured into ether (200 milliliter). The ether layer was extracted with 1 normal HCl (2×100 milliliter). The combined acidic layers were made alkaline with 10% ammonium hydroxide and extracted with methylene chloride (3×100 milliliter). The combined methylene chloride layers were dried (anhydrous MgSO$_4$), filtered and concentrated under vacuum to afford (±)-2-(benzyloxycarbonyl)-3-phenyl-4-amino-2-azabicyclo[3.3.1]nonane as yellow oil (0.36 grams, 57%).

$^1$H-NMR (CDCl$_3$) δ1.3–2.4 (9H, m), 3.4 (1H, d, J=8 Hz), 4.32 (1H, bs), 4.9–5.1 (2H, m), 5.33 (1H, d, J=8 Hz), 7.0–7.4 (10H, m).

H. (±)-3-phenyl-4-(2-methoxybenzyl)amino-2-azabicyclo[3.3.1]nonane 2-(benzyloxycarbonyl)-3-phenyl-4-amino-2-azabicyclo[3.3.1]nonane (0.36 gram, 1.0 millimole) was dissolved in methanol (10 milliliter) and the pH of the medium was adjusted to 5 with the help of methanolic HCl. Crushed 4 A° molecular sieves (~1.0 gram), sodium cyanoborohydride (66 mgs, 1.0 millimole) and o-methoxy benzaldehyde (0.167 gram, 1.2 millimole) were added and the resulting reaction mixture was stirred at room temperature for 16 hours. At the end of this period, the reaction mixture was filtered through diatomaceous earth (Celite (trademark)) and the filtrate was taken up in aq. ammonium hydroxide. The aqueous phase was extracted with methylene chloride (3×60 milliliter) and dried (anhydrous MgSO$_4$). The solvents were removed under reduced pressure to afford an oily residue (0.56 gram). This was dissolved in ethanol (20 milliliter) and to it 10% palladium on carbon (0.56 gram) and ammonium formate (0.56 gram) were added. The resulting reaction mixture was stirred at 25° C. for 4 hours. At the end of this period, the reaction mixture was filtered through diatomaceous earth (Celite (trademark)) which was washed with ethanol (50 milliliter) and methylene chloride (100 milliliter). The solvents were removed under vacuum to afford solid which was taken up in aqueous ammonium hydroxide and extracted with methylene chloride (3×60 milliliter). The organic extracts were combined and dried (anhydous MgSO$_4$). Evaporation of the solvents under reduced pressure afforded a yellow oil (331 mgs). This on treatment with ether-HCl a afforded yellow gummy salt which on crystallization from methanol-ethyl acetate afforded analytically pure (±)-3-phenyl-4-(2-methoxybenzyl)amino-2-azabicyclo[3.3.1]nonane dihydrochloride (124 mg, 30%). The structure was further confirmed by single crystal X-ray crystallographic analysis.

M.p. 241° C. (dec., HCl salt).

$^1$H-NMR (CDCl$_3$) δ1.38 (1H, dt, J=2.0, 12.4 Hz), 1.7–2.4 (10H, m) 2.71 (1H, t, J=3 Hz), 3.31 (2H, mdd, J=13.7 Hz), 3.31 (3H, s), 3.61 (1H, d, J=13.7 Hz), 4.84 (1H, d, J=3.7 Hz), 6.66 (1H, d, J=8 Hz), 6.79 (1H, dt, J=1.0, 7.5 Hz), 7.93 (1H, dd, J=1.5, 7.5 Hz), 7.1–7.4 (6H, m).

$^{13}$C-NMR (CDCl$_3$) δ21.3, 27.3, 27.8, 29.3, 32.1, 46.9, 47.3, 57.7, 60.1, 109.8, 119.9, 126.5, 127.8, 128.2, 128.3, 129.7, 142.3, 156.6.

C$_{22}$H$_{28}$N$_2$O.2HCl.0.5CH$_3$OH: C, 63.52; H, 7.58; N, 6.58. Found: C, 63.29; H, 7.49; N, 6.52.

I claim:
1. A compound of the formula

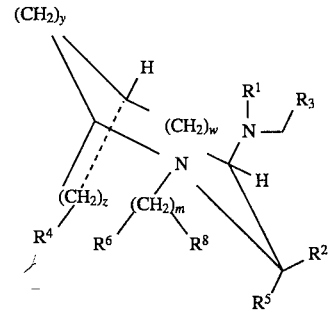

I wherein m is an integer from 0 to 8, and any one of the carbon-carbon single bonds of (CH$_2$)$_m$ may optionally be replaced by a carbon-carbon double bond or a carbon-carbon triple bond, and any one of the carbon atoms of said (CH$_2$)$_m$ may optionally be substituted with R$^8$;

w is an integer from 0 to 2;

y is an integer from 1 to 4;

z is an integer from 1 to 4, and wherein any one of the carbon atoms of said (CH$_2$)$_z$ may optionally be substituted with R$^4$;

R$^1$ is hydrogen or (C$_1$–C$_8$) alkyl optionally substituted with hydroxy, alkoxy or fluoro;

$R^2$ is a group selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; phenyl$(C_2-C_6)$ alkyl, benzhydryl and benzyl, wherein one of the phenyl moieties of said benzhydryl may optionally be replaced by naphthyl, thienyl, furyl or pyridyl, and wherein each of said aryl and heteroaryl groups and the phenyl moieties of said benzyl, phenyl$(C_2-C_6)$alkyl and benzhydryl may optionally be substituted with one or more substituents independently selected from halo, nitro, $(C_1-C_6)$alkyl, $(C_1-C_6)$alkoxy, trifluoromethyl, amino, $(C_1-C_6)$-alkylamino,

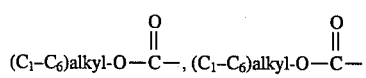

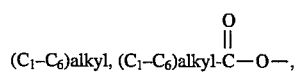

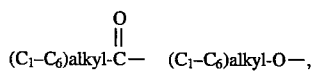

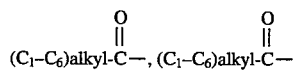

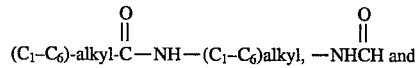

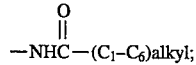

and wherein one of the phenyl moieties of said benzhydryl may optionally be replaced by naphthyl, thienyl, furyl or pyridyl;

$R^5$ is hydrogen, phenyl or $(C_1-C_6)$alkyl;

or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;

$R^3$ is aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; or cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, each of said substituents being independently selected from halo, nitro, $(C_1-C_6)$alkyl optionally substituted with from one to three fluorine atoms, $(C_1-C_6)$alkoxy optionally substituted with from one to three fluorine atoms, phenyl, amino, $(C_1-C_6)$alkylamino, $(C_1-C_6)$ dialkylamino,

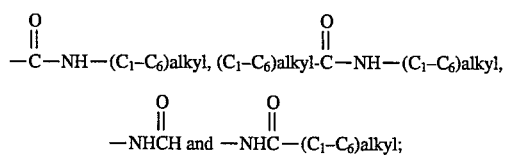

$R^4$ is independently selected from hydrogen, hydroxy, halo, amino, oxo (=O), nitrile, $(C_1-C_6)$alkylamino, di-$(C_1-C_6)$alkylamino, $(C_1-C_6)$alkoxy,

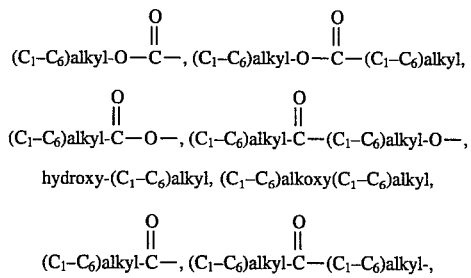

and the groups set forth in the definition of $R^2$;

$R^6$ is

$NHCH_2R^9$, $NHSO_2R^9$ or one of the groups set forth in any of the definitions of $R^2$ and $R^4$;

$R^8$ is oximino (=NOH) or one of the groups set forth in any of the definitions of $R^2$ and $R^4$;

$R^9$ is $(C_1-C_6)$alkyl, hydrogen, phenyl or phenyl $(C_1-C_6)$alkyl;

with the proviso that (a) when m is 0, $R^8$ is absent, (b) neither $R^4$, $R^6$, nor $R^8$ can form, together with the carbon to which it is attached, a ring with $R^5$, and (c) the sum of y and z must be less than 7.

2. A compound according to claim 1 wherein m, w, y, z, $R^3$, $R^4$, $R^5$, $R^6$ and $R^8$ are defined as in claim 1 and $R^2$ is a radical selected from hydrogen, phenyl, naphthyl and benzhydryl; wherein each of said phenyl, naphthyl and benzhydryl may optionally be substituted with one or more substituents independently selected from halo, nitro, $(C_1-C_6)$ alkyl, $(C_1-C_6)$alkoxy, trifluoromethyl, amino, $(C_1-C_6)$-alkylamino,

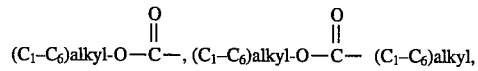

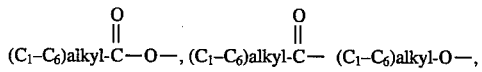

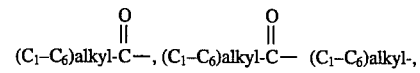

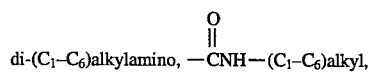

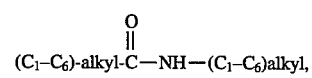

and wherein one of the phenyl moieties of said benzhydryl may optionally be replaced by naphthyl, thienyl, furyl or pyridyl.

3. A compound according to claim 1 wherein m, w, y, z, $R^3$, $R^5$, $R^6$ and $R^8$ are defined as in claim 1 and $R^2$ is a group selected from hydrogen, phenyl, naphthyl and benzhydryl; wherein each of said phenyl, naphthyl and benzhydryl may optionally be substituted with one or more substituents independently selected from halo, nitro, $(C_1-C_6)$ alkyl, $(C_1-C_6)$ alkoxy, trifluoromethyl, amino, $(C_1-C_6)$-alkylamino, $(C_1-C_6)$alkyl-O—$\overset{\overset{O}{\|}}{C}$—, $(C_1-C_6)$alkyl-O—$\overset{\overset{O}{\|}}{C}$— $(C_1-C_6)$alkyl, $(C_1-C_6)$alkyl-$\overset{\overset{O}{\|}}{C}$—O—, $(C_1-C_6)$alkyl-$\overset{\overset{O}{\|}}{C}$— $(C_1-C_6)$alkyl-O—, $(C_1-C_6)$alkyl-$\overset{\overset{O}{\|}}{C}$—, $(C_1-C_6)$alkyl-$\overset{\overset{O}{\|}}{C}$— $(C_1-C_6)$alkyl-, di-$(C_1-C_6)$alkylamino, —$\overset{\overset{O}{\|}}{C}$NH—$(C_1-C_6)$alkyl, $(C_1-C_6)$-alkyl-$\overset{\overset{O}{\|}}{C}$—NH—$(C_1-C_6)$alkyl, —NH$\overset{\overset{O}{\|}}{C}$H and —NH$\overset{\overset{O}{\|}}{C}$—$(C_1-C_6)$alkyl;

and wherein one of the phenyl moieties of said benzhydryl may optionally be replaced by naphthyl, thienyl, furyl or pyridyl; and $R^4$ is independently selected from hydrogen, hydroxy, halo, amino, oxo (=O), nitrile, $(C_1-C_6)$alkylamino, di-$(C_1-C_6)$alkylamino, $(C_1-C_6)$alkoxy, $(C_1-C_6$alkyl-O—$\overset{\overset{O}{\|}}{C}$—, $(C_1-C_6)$alkyl-O—$\overset{\overset{O}{\|}}{C}$—$(C_1-C_6)$alkyl, $(C_1-C_6)$alkyl-$\overset{\overset{O}{\|}}{C}$—O—, $(C_1-C_6)$alkyl-$\overset{\overset{O}{\|}}{C}$—$(C_1-C_6)$alkyl-O—, hydroxy-$(C_1-C_6)$alkyl, $(C_1-C_6)$alkoxy$(C_1-C_6)$alkyl $(C_1-C_6)$alkyl-$\overset{\overset{O}{\|}}{C}$—, $(C_1-C_6$alkyl-$\overset{\overset{O}{\|}}{C}$—$(C_1-C_6)$alkyl-, $(C_1-C_6)$alkyl and phenyl.

4. A compound according to claim 2, wherein said compound is (3RS, 4RS)-3-phenyl-4-(2-methoxybenzyl)amino-2-azabicyclo[3.3.1]nonane.

5. A compound of the formula

IV wherein w is an integer from 0 to 2;
y is an integer from 1 to 4;
z is an integer from 1 to 4, and wherein any one of the carbon atoms of said $(CH_2)_z$ may optionally be substituted with $R^4$;
$R^2$ is a group selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; phenyl$(C_2-C_6)$alkyl, benzhydryl and benzyl, wherein one of the phenyl moieties of said benzhydryl may optionally be replaced by naphthyl, thienyl, furyl or pyridyl, and wherein each of said aryl and heteroaryl groups and the phenyl moieties of said benzyl, phenyl$(C_2-C_6)$alkyl and benzhydryl may optionally be substituted with one or more substituents independently selected from halo, nitro, $(C_1-C_6)$alkyl, $(C_1-C_6)$alkoxy, trifluoromethyl, amino, $(C_1-C_6)$-alkylamino, $(C_1-C_6)$alkyl-O—$\overset{\overset{O}{\|}}{C}$—, $(C_1-C_6)$alkyl-O—$\overset{\overset{O}{\|}}{C}$— $(C_1-C_6)$alkyl, $(C_1-C_6)$alkyl-$\overset{\overset{O}{\|}}{C}$—O—, $(C_1-C_6)$alkyl-$\overset{\overset{O}{\|}}{C}$— $(C_1-C_6)$alkyl-O—, $(C_1-C_6)$alkyl-$\overset{\overset{O}{\|}}{C}$—, $(C_1-C_6)$alkyl-$\overset{\overset{O}{\|}}{C}$— $(C_1-C_6)$alkyl-, di-$(C_1-C_6)$alkylamino, —$\overset{\overset{O}{\|}}{C}$NH—$(C_1-C_6)$alkyl, $(C_1-C_6)$-alkyl-$\overset{\overset{O}{\|}}{C}$—NH—$(C_1-C_6)$alkyl, —NH$\overset{\overset{O}{\|}}{C}$H and —NH$\overset{\overset{O}{\|}}{C}$—$(C_1-C_6)$ alkyl;

and wherein one of the phenyl moieties of said benzhydryl may optionally be replaced by naphthyl, thienyl, furyl or pyridyl;

$R^5$ is hydrogen, phenyl or $(C_1-C_6)$alkyl;

or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;

$R^4$ is independently selected from hydrogen, hydroxy, halo, amino, oxo (=O), nitrile, $(C_1-C_6)$alkylamino, di-$(C_1-C_6)$alkylamino, $(C_1-C_6)$alkoxy, $(C_1-C_6)$alkyl-O—$\overset{\overset{O}{\|}}{C}$—, $(C_1-C_6)$alkyl-O—$\overset{\overset{O}{\|}}{C}$—$(C_1-C_6)$alkyl, $(C_1-C_6)$alkyl-$\overset{\overset{O}{\|}}{C}$—O—, $(C_1-C_6)$alkyl-$\overset{\overset{O}{\|}}{C}$—$(C_1-C_6)$alkyl-O—, hydroxy-$(C_1-C_6)$alkyl, $(C_1-C_6)$alkoxy$(C_1-C_6)$alkyl, $(C_1-C_6)$alkyl-$\overset{\overset{O}{\|}}{C}$—, $(C_1-C_6)$alkyl-$\overset{\overset{O}{\|}}{C}$—$(C_1-C_6)$alkyl-, and the groups set forth in the definition of $R^2$.

6. A compound according to claim 5, wherein said compound is (3RS,4RS)-2-(benzyloxycarbonyl)-3-phenyl-4-amino-2-azabicyclo[3.3.1]nonane.

7. A pharmaceutical composition for treating or preventing a condition selected from the group consisting of inflammatory diseases, anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in preventing or treating such condition and a pharmaceutically acceptable carrier.

8. A method of treating or preventing a condition selected from the group consisting of inflammatory diseases anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, disorders related to immune enhancement or suppression and rheumatic diseases in a mammal, comprising administering to a mammal in need of such treatment or prevention an amount of a compound according to claim 1 effective in preventing or treating such condition.

9. A pharmaceutical composition for antagonizing the effects of substance P in a mammal, comprising a substance P antagonizing effective amount of a compound according to claim 1 and a pharmaceutically acceptable carrier.

10. A method of antagonizing the effects of substance P in a mammal, comprising administering to said mammal a substance P antagonizing effective amount of a compound according to claim 1.

11. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

12. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

13. A pharmaceutical composition for treating or preventing a condition in a mammal, the treatment or prevention of which is effected or facilitated by a decrease in substance P mediated neurotransmission, comprising an amount of a compound according to claim 1, or a pharmaceutically acceptable salt thereof, effective in treating or preventing such condition and a pharmaceutically acceptable carrier.

14. A method of treating or preventing a condition in mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

* * * * *